United States Patent
Akeel et al.

(12)

(10) Patent No.: US 9,675,419 B2
(45) Date of Patent: Jun. 13, 2017

(54) SYSTEM AND METHOD FOR AUTOMATING MEDICAL PROCEDURES

(71) Applicant: Brachium Labs, LLC, San Ramon, CA (US)

(72) Inventors: Hadi Akeel, Bloomfield Hills, MI (US); Yaz Shehab, San Francisco, CA (US); George Wong, San Ramon, CA (US)

(73) Assignee: Brachium, Inc., San Francisco, CA (US)

( * ) Notice: Subject to any disclaimer, the term of this patent is extended or adjusted under 35 U.S.C. 154(b) by 680 days.

(21) Appl. No.: 13/972,273

(22) Filed: Aug. 21, 2013

(65) Prior Publication Data

US 2015/0057675 A1 Feb. 26, 2015

(51) Int. Cl.
*A61B 19/00* (2006.01)
*G06F 19/00* (2011.01)
(Continued)

(52) U.S. Cl.
CPC .............. *A61B 19/50* (2013.01); *A61B 34/10* (2016.02); *A61B 34/30* (2016.02); *A61B 34/32* (2016.02);
(Continued)

(58) Field of Classification Search
CPC .... A61C 1/00; A61C 5/02; A61C 5/08; A61C 7/002; A61C 7/146; A61C 8/0089;
(Continued)

(56) References Cited

U.S. PATENT DOCUMENTS

| 5,224,049 A | * | 6/1993 | Mushabac | .......... | G05B 19/4207 |
| | | | | | 264/222 |
| 5,343,391 A | | 8/1994 | Mushabac | | |

(Continued)

OTHER PUBLICATIONS

The Journal of the American Dental Association, "Robotics in Dentistry," Aug. 2001, vol. 132, No. 8, p. 1095.
(Continued)

*Primary Examiner* — Dale Moyer
(74) *Attorney, Agent, or Firm* — Shumaker Loop & Kendrink; William J. Clemens (57) ABSTRACT

A system and a method for automating a medical process including a memory storing a software program, a computer connected to the memory for running the software program, a display connected to the computer for generating a visual representation of output data generated by the computer running the program, a user interface connected to the computer for obtaining image data representing a configuration of a patient treatment space and fixed markers in the treatment space and storing the image data in the memory, a robot arm connected to the computer, and a medical tool mounted on the robot arm wherein when a human inputs a selected treatment procedure into the computer, the computer runs the software program to generate a tool path based upon the treatment procedure and the image data, and the computer operates the robot arm to move the medical tool along the tool path without human guidance, and wherein the data generated during the treatment procedure is stored, analyzed, and shared among collaborating computer systems.

24 Claims, 4 Drawing Sheets

(51) Int. Cl.
| | | |
|---|---|---|
| *A61C 7/00* | (2006.01) | |
| *A61C 7/14* | (2006.01) | |
| *A61C 8/00* | (2006.01) | |
| *A61C 17/00* | (2006.01) | |
| *A61C 1/00* | (2006.01) | |
| *A61B 34/32* | (2016.01) | |
| *A61B 34/30* | (2016.01) | |
| *A61C 5/40* | (2017.01) | |
| *A61C 5/70* | (2017.01) | |
| *A61C 3/02* | (2006.01) | |
| *A61G 15/14* | (2006.01) | |
| *A61B 34/10* | (2016.01) | |
| *A61B 90/00* | (2016.01) | |
| *A61B 34/20* | (2016.01) | |
| *A61B 34/00* | (2016.01) | |

(52) U.S. Cl.
CPC .............. *A61C 1/00* (2013.01); *A61C 5/40* (2017.02); *A61C 5/70* (2017.02); *A61C 7/002* (2013.01); *A61C 7/146* (2013.01); *A61C 8/0089* (2013.01); *A61C 17/00* (2013.01); *G06F 19/3406* (2013.01); *G06F 19/3437* (2013.01); *A61B 2034/102* (2016.02); *A61B 2034/105* (2016.02); *A61B 2034/107* (2016.02); *A61B 2034/2065* (2016.02); *A61B 2034/252* (2016.02); *A61B 2090/3612* (2016.02); *Y10S 901/09* (2013.01); *Y10S 901/47* (2013.01)

(58) Field of Classification Search
CPC . A61C 17/00; G06F 19/3406; G06F 19/3437; A61B 2576/00; A61B 2217/00
See application file for complete search history.

(56) References Cited

U.S. PATENT DOCUMENTS

| | | | | |
|---|---|---|---|---|
| 5,347,454 A | * | 9/1994 | Mushabac | G05B 19/4207 433/214 |
| 5,448,472 A | * | 9/1995 | Mushabac | A61C 13/0004 433/70 |
| 5,545,039 A | * | 8/1996 | Mushabac | A61C 13/0004 433/215 |
| 5,562,448 A | * | 10/1996 | Mushabac | A61C 13/0004 433/215 |
| 6,532,299 B1 | | 3/2003 | Sachdeva et al. | |
| 6,640,128 B2 | | 10/2003 | Vilsmeier et al. | |
| 6,801,913 B2 | | 10/2004 | Matsumura et al. | |
| 7,455,520 B2 | | 11/2008 | Sorensen et al. | |
| 7,625,208 B2 | | 12/2009 | Warner | |
| 7,742,635 B2 | | 6/2010 | Rohaly et al. | |
| 7,907,166 B2 | | 3/2011 | Lamprecht et al. | |
| 8,095,200 B2 | | 1/2012 | Quaid, III | |
| 8,416,984 B2 | | 4/2013 | Liang et al. | |
| 2001/0051881 A1 | * | 12/2001 | Filler | G06F 19/322 705/3 |
| 2002/0064759 A1 | | 5/2002 | Durbin et al. | |
| 2002/0077542 A1 | | 6/2002 | Vilsmeier et al. | |
| 2005/0186533 A1 | | 8/2005 | Cohen | |
| 2007/0172803 A1 | | 7/2007 | Hannaford et al. | |
| 2008/0081982 A1 | * | 4/2008 | Simon | G06F 19/3437 600/407 |
| 2010/0017032 A1 | | 1/2010 | Dai et al. | |
| 2011/0039229 A1 | | 2/2011 | Senia | |
| 2011/0256496 A1 | | 10/2011 | Arzanpour | |
| 2012/0190981 A1 | | 7/2012 | Harris et al. | |
| 2012/0231421 A1 | | 9/2012 | Boerjes et al. | |
| 2012/0253360 A1 | | 10/2012 | White et al. | |
| 2013/0039541 A1 | | 2/2013 | Inazumi | |

OTHER PUBLICATIONS

Xiaoyan Sun, et al., "Automated Dental Implantation Using Image-Guided Robotics: Registration Results," Int J CARS, 2001, vol. 6, pp. 627-634.

Allen Daniels, "The Future of Cosmetic Dentistry," Mar. 16, 2010, Retrieved from the Web: <guidetodentistry.com/the-future-of-cosmetic-dentistry/>.

The SensAble Dental Lab System Flyer, SensAble Techonologies, www.sensable.com, Copyright 2007.

* cited by examiner

SYSTEM AND METHOD FOR AUTOMATING MEDICAL PROCEDURES

FIELD OF THE INVENTION

The invention relates to a system and a method for automating medical treatment procedures and augmenting the intellectual effort of the medical professional by the physical work of computer controlled machines and manipulators.

BACKGROUND OF THE INVENTION

Medical procedures include surgical, dental and health treatments. Medical procedures are performed either manually or with the assistance of supportive technologies for the enhancement of data collection, examination, visualization, or dexterity.

Medical treatment procedures such as surgeries and dental implants are carried out mostly manually, wherein the medical professional manipulates surgical tools for performing complex surgical and restoration procedures. The procedures can also be performed manually but with the help of a variety of supportive technologies that augment the professional's ability to examine the patient and observe the conditions of the ailment.

The professional relies on his or her medical expertise, manual dexterity, and hand-eye coordination skills to perform the procedures. Such skills and expertise vary widely among professionals and the results of the procedures are not always equivalent. To improve the success rate of a procedure, the professional makes use of data from laboratory and physical tests, detectable characteristics and by observation. X-rays provide visual details unavailable to the naked eye. Such data helps the professional decide on a treatment approach that, in his or her professional judgment, is best for the patient; that is not usually verified until after the procedure is completed with occasional unfortunate surprises.

To enhance the chances of success, new technologies have been developed that augment the professional examination capabilities, collect more supportive data for the procedure, improve over the dexterous skills of the professional and greatly enhance the hand-eye coordination. Vision systems utilizing video cameras, some miniature, can provide visual observations in tight locations and often are inserted into the human body cavities for real time examinations and collection of otherwise inaccessible information. Alternatively, technology has developed that often separated the professional from the patient. The professional's vision is augmented by tiny video cameras inserted into the treatment space. Dexterous skills are augmented by inserting miniature manipulators into the treatment space to manipulate the instruments. The cameras and the instruments are remotely manipulated by the professional with access to a magnified view of the tiny treatment space and controlled resolution for hand movements.

A well-known navigation guided surgical system, the da Vinci® Surgical System available from Intuitive Surgical of Sunnyvale, Calif., has been very successful in aiding surgeons perform complex minimally invasive procedures. With that system, complex surgeries are performed by remotely manipulating several surgical instruments inserted into the human body through minimal surgical cuts and attached to multi-axis computer controlled manipulators. It utilizes remotely controlled robotic arms carrying surgical instruments and visualization cameras that are manipulated by the surgeon from a remote control console. It provides enhanced visualization of the treatment space and better operational dexterity by beneficially utilizing digital scaling of images and instrument movements. It has enabled many procedures to be performed more successfully with less exposure to trauma by the patients.

Surgery could even be performed from remote locations by communicating the images of the work space in real time to distant locations where a surgeon can remotely guide and manipulate a surgical tool that is attached to a computer controlled manipulator.

Recently, surgical procedures have benefitted from new advances in imaging of the treatment space, computerized solid modeling technique and interactive graphics. The treatment space can now be scanned, digitally modeled, projected at a larger scale, and visualized from angles almost inaccessible to conventional visualization means. The surgical procedures can be pre-planned by interactively manipulating digitized virtual models of the treatment space and recording a desired procedure. Critical progress parameters can be displayed to guide the medical professional through the surgical process as described in the U.S. Pat. No. 6,640,128 B2 (the '128 patent). Tiny video cameras can be strategically located to monitor the treatment space, display the progress of the procedure, or identify deviations from the pre-planned course; this also allows multiple professionals to observe and monitor the procedure's progress.

3-dimensional images are virtual models of an object or a space that can also be stored with attributes that allow projection and manipulation of the images on a display to be viewed from any desired angle. Interfaces are provided for interactive input devices to help modify or augment the model with additional information such as tracing a path for a tool or displaying specific characteristics of the model. The virtual model could also be communicated to computer controlled machine tools that extract data necessary for the fabrication of certain parts of the model (impression of a jaw) or can be complementary to certain model parts (crown for a tooth).

The applications described above utilize computer controlled manipulators that are responsive to manipulation commands initiated by the medical professional. The manipulators do not utilize the ability of a robot to perform autonomous operations and are dependent on continuous interaction by the professional. In a manner similar to a machine tool, a robot was demonstrated at the University of California, Santa Cruz, Bionics Lab, spring 2011, for the milling of a model tooth in preparation for the addition of a crown; that was not a medical application as much as a demonstration of machining by a robot rather than by a conventional machine tool.

A method and device for navigation-assisted dental treatment is described in the '128 patent, wherein an image of the treatment space is generated and displayed on a screen monitor to provide visual guidance to the dentist before, during, and after the procedure. Cameras are also provided to track markers in the treatment space as well as the dental instruments and help the dentist in visualizing their relative locations on the large screen instead of the confined space of a human jaw. The desired path of the treatment instrument is also displayed together with the actual path traced by the dentist and a warning signal is generated when the two paths deviate. The '128 patent also recognizes that a robot can be used to guide the instrument during the treatment; the instrument's location is registered, tracked and controlled by the system.

However, the '128 patent is limited to "navigation assisted dental treatment" and does not extend to relieving the dentist from performing manual or dexterous operations. The imaging system serves to provide visualization of the treatment space and the relative position of the instruments during the process and leaves it to the dentist to manipulate the instruments. The procedure is then still subject to the limitations of the dentist's skills and dexterity. It teaches no autonomous operation. It teaches that the tracking system tracks the position of the instrument during the procedure and warns when the location deviates from a desired path; it displays a corrected path but leaves it to the dentist to respond. The '128 patent also recognizes the use of a robot "which fully or partly guides the instrument, is registered and/or referenced in the navigation and/or tracking system and positionally tracked, and is controlled by the system", but it does not teach the source of information that the robot is guided by and does not relate it's operation to the digital data set of the treatment space.

Image-guided navigation in restorative dentistry and oral maxillofacial surgery: Dental imaging systems have been used to generate a virtual image of the treatment space, the jaw, and the teeth that is utilized to plan for the treatment and the fabrication of prosthetic devices such as crowns and implants. Such imaging systems today can be exemplified by commercially available products such as: the NobelGuide system available from Nobel Biocare USA, LLC of Yorba Linda, Calif.; the Anatomage imaging software available from Anatomage Inc. of San Jose, Calif.; Sirona CEREC CAD/CAM system available from Sirona Dental Systems LLC of Charlotte, N.C.; the Lava COS system available from 3M ESPE of St. Paul, Minn.; the iTero imaging system available from Align Technology, Inc. of San Jose, Calif.; and the TRIOS Digital Impression Taking Solution from 3Shape A/S, Copenhagen, Denmark.

For example, the image can be communicated to a milling machine or a 3 D printer for the fabrication of a mold or an artificial tooth, a crown or bridge. Currently, on-site and off-site milling capabilities are available from commercial entities such as: Sirona Dental Systems; 3M ESPE; Nobel Biocare; Henry Schein Inc. of Melville, N.Y.; Dentsply Implants of Waltham, Mass.; Dental Wings, Inc. of Montreal, Canada.

The crown or bridge can be very accurately fabricated and provide a consistent and unusually good fit to the tooth for much higher longevity than with manually prepared and fitted crowns. Manually prepared teeth and fitted crowns introduce human errors at several stages, from not creating the stone models correctly, not trimming the model dies correctly, to not casting the metal substructures accurately. Final fitting of the crown or bridge by the dentist will also determine if the restorations will achieve a high level of marginal fit.

Even with the availability of imaging and navigation systems, much of the manual work is still done by the dentist, e.g. tooth preparation is done by milling the tooth with a handheld mill at the risk of under/over cuts and possible injury to healthy tissue or enamel. The level of difficulty increases by a multiple for a dental bridge where multiple teeth in the mouth have to be milled in parallel with slight six degrees of taper to create a proper path of insertion. All of the teeth prepared for a dental bridge must share a common long axis ideally. Manual operations are lengthy procedures and cause appreciable discomfort and stress to the patients. It's also common in dental drilling and burring procedures to encounter zones of differing substrate hardness that causes the rotational speed of the tool to increase or decrease. This is usually caused when the instrument encounters softer or harder tissues in its path. If sensed and reacted to quickly, the dentist can either stop drilling into healthy enamel or proceed further to remove unhealthy tissue respectively. It is therefore desirable to have means to sense changes in the hardness of the tissue and automatically respond without relying on human senses and reaction. The dentist also can use his or her finger to feel and respond to occasional movements by the patient; a more reliable sensing means is, of course, advantageous.

In Orthodontic Treatment, such as the attachment of orthodontic braces brackets, the placement of the brackets has traditionally been done by mixing cement and placing it into the bonding surface of the bracket. Current cements are UV cured or self-curing. The amount of cement can vary and the excess cement must be removed manually without touching the bracket. Removal of the cement and accidentally moving the bracket in the process creates a source of positional error. The accuracy is dependent on the dexterity by the orthodontist. Inadequate metering of the cement adversely changes the position of the bracket.

Anesthesia is delivered in the form of a mandibular nerve block. The mandibular nerve has to be approximated by the dentist at the entry point of where it enters the mandible. The anesthesia then has to be manually delivered and if delivered too quickly, localized pressure from the anesthesia can produce discomfort to the patient.

For dental implants, CT Scanning and 3D modeling are commonly used in implant treatment planning and surgical guides are created by manufacturers. The surgical guides are placed directly on the soft gum tissue and stabilized by hand or guide pins placed into the bone. The gum tissue can move during surgery introducing errors. In dental bridges supported by multiple implants, all implants ideally must share a common long axis, or additional angulated parts, which are needed for connecting the angulations, thereby increasing treatment costs.

Current root canal treatment systems involve cleaning the internal canals in the root system to remove any infected tissue present. Laser treatment or other treatment modalities delivered through fiber optics can clean the canals in a radial and 3D manner that the reamer tools currently used cannot. The completion of the root canal is filling the canal with a sealant and gutta percha which is a rubber like material that fills the canal preventing bacteria from passing through the root system into the jaw bone. This gutta-percha is flowable when warmed to a determined temperature and solidifies into a solid 3D structure forming a comprehensive seal.

It's important to determine the depth of the apex and inject the warmed gutta percha material precisely to prevent extrusion of material through the apex or under-filling the canal by accident.

Oral Surgery Procedures: a tooth extraction is performed by pulling and elevation of a tooth under pressure. Occasionally, the dentist may have to drill the entire tooth from the socket with a risk of injury to vital structures such as a nearby nerve causing permanent nerve damage to the patient; a more reliable procedure is desirable.

However, the current support given to the medical and dental professional only provides enhanced visualization, a pre-planning platform, and monitoring means. The actual procedure is usually done by the professional either by remote control or physically by personally manipulating the instruments, or manipulating instruments with guides. This direct manipulation by the professional makes it subject to human errors and the limitations of the professional's skill and manual dexterity; manual accuracy is seriously limited and occasional mistakes and missteps do occur. Such mistakes may cause harm to the patient and sizable financial liabilities for patient, healthcare provider and insurer.

Direct manipulation of the instruments by the professional also demands appreciable care to mitigate the risk of mistakes and is inherently a slow process; it exposes the patient to increased stress as the procedure duration extends. This is especially critical for the metered delivery of drugs, such as anesthesia, that requires accurate metering of the rate of delivery and requires high level of experience.

Currently information associated with medical procedures is tracked locally in each treatment facility, mostly manually or with paper documents. Data of diagnoses, procedures, tools, materials, and outcomes are not usually communicated between treatment locations. This does not lend itself to data mining that may help practitioners share experiences, improve procedures and benefit patients from the data.

Delivery of materials, such as anesthetics, chemotherapy agents, require precise metering and location relative to anatomical landmarks. This is currently subject to indefinite identification of the location and human dexterity inaccuracies.

Soft tissue has anatomical mobile landmarks. Medical instruments and procedures, which interact with this soft tissue have issues of accuracy in locating the desired targets. Procedures such as drawing blood, spinal taps, and needle biopsies of tumors near vital structures, etc., require a high level precision and dexterity that are subject to uncertainty because of tissue mobility.

Most medical treatment procedures, especially surgeries, are performed by medical professionals manually according to pre-set plans for each procedure. The procedure is then carried out by the professional who depends on his/her experience and memory to either follow or modify the procedure during the treatment. There is much risk involved here especially if experience is lacking and decisions are made under pressure. This subjects the professional to appreciable stress in making serious decisions while the welfare of a human being is at stake.

SUMMARY OF THE INVENTION

It is therefore desirable to provide an enhanced medical treatment system that utilizes the professional knowledge of the medical professional for deciding what to do in a procedure and how to do it and is not dependent on his/her manipulative skills or dexterity.

It is also desirable to provide an enhanced treatment system that can be performed autonomously according to a pre-planned and verified approach, hence with minimum duration and most comfort to the patient.

It is also desirable to provide an enhanced treatment system having the accuracy and reliability of computer controlled manipulators to improve medical procedures outcome.

It is also desirable to provide an enhanced treatments system that accurately controls the performance of the instruments used in medical procedures including drug delivery instruments.

It is also desirable to provide an enhanced treatment system that allows in-process accurate measurements of critical process parameters and assure its progress according to prior plans.

It is desirable to provide a treatment procedure that allows professional decisions be made and tested off-line and the outcome verified without the pressures of real time operations. Hence, allowing the professional to make correct decisions and pre-plan the treatment in its best form as well as allow the treatment to be performed without deviation from the planned course.

It is therefore desirable to have a medical treatment system that tracks patient diagnosis data, provider data, procedure data, parts used in procedures, and procedure outcomes. The system securely stores this data to be accessed at a future time on a local and/or centralized storage system. The system makes this data available to providers for future treatments and data research. This data facilitates new procedures performed on a patient during the course his/her lifetime. Each system communicates its data over a network with other systems and practitioners.

The system uses the collected data, along with treatment outcomes and other external data to inform the practitioners, suppliers, etc. to make adaptive treatment procedure decisions. The system also has an intelligent adaptive learning capacity to provide relevant data mining to inform procedures, research and statistical data and generate recommendations for enhancements to the procedures. The system communicates with other systems, peripherals, devices and shareable databases via centrally located and networked communications networks.

It is desirable to have a system that delivers materials, such as anesthetics, chemotherapy agents with precise metering and location relative to anatomical landmarks.

It is desirable to have a system that is adaptive to the mobility of soft tissue for conducting procedures, such as drawing blood, spinal taps, and needle biopsies of tumors near vital structures, etc., with precision and high level of dexterity.

Accordingly, objects of the system according to the invention include:

1) Relieve the professional from direct manipulation of surgical instruments.
2) Provide an enhanced treatment system that can be performed autonomously, hence with best quality, minimum duration, and most comfort to the patient.
3) Provide an enhanced medical treatment system that utilizes the intellectual knowledge of the medical professional for deciding what to do in a procedure and is not dependent on his/her manipulative skills or dexterity.
4) Provide a treatment process that can be pre-planned and verified and allows the making of professional decisions off-line without the pressures of real time operations.
5) Provide a treatment process that optimizes the use of professional knowledge and the precision of computerized manipulators to perfect a medical procedure.
6) Provide a treatment system that can detect and respond to changes in process parameters such a tool's performance and treatment space movements.
7) Provide a treatment system that can precisely control the performance of the treatment delivery instruments especially drug delivery instruments.
8) Provide a treatment system that includes in process measurement of critical process parameters to assure its progress integrity according to prior plans.
9) Provide a treatment system capable of delivery of materials, such as anesthetics, chemotherapy agents, that require precise metering and location relative to anatomical landmarks.
10) Provide a treatment system that tracks and stores data associated with a procedure for possible sharing among professionals, analysis by intelligent learning systems, and, generation of enhancements to the procedures based on the shared experiences.

Some system advantages are illustrated best in dental applications as follows:

1) A highly adaptive system that can be used for dental and medical purposes,
2) Since the path and final milling shape of the tooth is pre-determined, the crown can be prepared before the tooth is cut. This results in significant reduction in the time required for crown preparation procedures.
3) Since the milled tooth and the crown are extremely accurate, the fit of the final restoration will be exceptional, thus increasing the lifetime of the crown, and reducing replacement costs.
4) Since the system can cut a tooth more accurately than a human, and the path is traced and predetermined by software, accidental cutting of adjacent teeth and tissue is avoided.
5) Shorter procedure time and increased patient comfort and trust due to robotic accuracy.
6) An orthodontist can pre-plan a more precise placement of the brackets and the exact amount of required cement adhesive from a scan with much greater accuracy.
7) For surgical implants the treatment space tracking approach removes the need for a surgical guide. The system places the implants precisely with controlled torque and rpms as specified by the implant manufacturers.

A system for automating a medical process according to the invention comprises: a memory storing a software program; a computer connected to the memory for running the software program; a display connected to the computer for generating a visual representation of output data generated by the computer running the program; a user interface connected to the computer for obtaining image data representing a configuration of a patient treatment space and fixed markers in the treatment space and storing the image data in the memory; a robot arm connected to the computer; and a medical tool manipulated by the robot arm wherein when a human inputs a selected treatment procedure into the computer, the computer runs the software program to generate a tool path based upon the treatment procedure and the image data, and the computer operates the robot arm to move the medical tool along the tool path without human guidance.

A plurality of sensors are mounted on the medical tool providing location feedback to the computer representing a position of the medical tool relative to the markers, and the sensors can be one or more cameras, tactile sensors or other types. The computer alters the tool path in response to movement in the treatment space detected in the image feedback of the cameras or signals from other sensors. The computer can also actively compare surface textures and overlay them mathematically to compare its position for accuracy. The cameras also generate an image of the treatment space.

The user interface can be a display showing the virtual image and input devices for manipulating and modifying the virtual image. Any input device capable of interacting through the computer can be used. The user interface also includes conventional devices used with robots such as teach pendants for jogging the robot and recording path and process data. It may also include other pendants or joy sticks operative to guide the robot by remotely throughout the procedure (remote control) or during part of the procedure while other parts of the procedure are performed autonomously (hybrid control). In hybrid control, the professional may lead the robot to the start of the procedure and let the computer take over to the end or to a defined step of the process whereas the professional takes over again and remotely guides the robot through other steps of the process.

The computer processes the image data to generate a virtual model of the treatment space. The virtual model is referenced to a local coordinate system based upon the configuration of the treatment space. A physical model may also be generated by an imprint of the treatment space or from the virtual model. The treatment space can be located in a patient's mouth and the treatment procedure is one of milling a tooth, drilling a tooth, installing a crown, installing an implant, or other commonly performed dental procedures.

The system can include a shut-off control connected to the computer and being responsive to actuation by a patient, or by a malfunction signal received by the computer from sensors, to stop the tool movement and withdraw the medical tool from the treatment space.

The system can include safeguards to guard against extraneous and intrinsic hazardous influences such as controls' malfunction or collisions with external objects.

The system includes a central data storage for sharing its data with other computer systems, for intelligent data mining, and for collaborative enhancement and analysis of shared treatment experiences.

A method of automatically performing a medical treatment procedure in a treatment space according to the invention comprises the steps of: operating an imaging system to obtain image data representing a configuration of a patient treatment space and fixed markers in the treatment space; generating a virtual/physical model of the treatment space; selecting a treatment procedure to be performed in the treatment space; generating a tool path for movement of a medical tool carried by a robot arm based upon the treatment procedure and the virtual/physical model; and actuating a computer to operate the robot arm to move the medical tool along the tool path thereby performing the treatment procedure.

The method includes generating the virtual/physical model as a multidimensional image of the treatment space. The virtual/physical model is referenced to a local coordinate system based upon the configuration of the treatment space. The method includes relating the local coordinate system to the fixed markers.

The method includes generating the tool path by overlaying a trace on the virtual image of the treatment space or leading the robot manually or by remote control within the physical model of the treatment space.

The method includes modifying the tool path during the procedure by the professional by remotely manipulating the robot and overriding the pre-planned tool path.

The treatment procedure can be one of dental applications, such as milling a tooth, drilling a tooth, installing a crown, installing orthodontic brackets, dental cleanings, root canals and installing an implant, or other medical procedures, such as delivery of materials, anesthetics, chemotherapy agents, drawing blood, spinal taps, and needle biopsies of tumors near vital structures, etc.

The method includes storing the tool path in a memory connected to the computer. The computer alters the tool path in response to movement in the treatment space detected by a tracking system. The method includes moving the medical tool to a vicinity of the treatment space, locating the markers and moving the medical tool to a start of the tool path based upon positions of the markers. The method includes locating the markers by one of touching the markers with the medical tool and by acquiring an image of the markers with a camera. The method also includes identifying surface textures, by the imaging systems as markers The method includes automatically withdrawing the medical tool from the treatment space at the end of the tool path to finish the treatment procedure. The method also includes displaying representations of the virtual/physical model and the tool path on a display connected to the computer.

DESCRIPTION OF THE DRAWINGS

The above as well as other advantages of the present invention will become readily apparent to those skilled in the art from the following detailed description of a preferred embodiment when considered in the light of the accompanying drawings in which.

DETAILED DESCRIPTION OF THE INVENTION

The following detailed description and appended drawings describe and illustrate various exemplary embodiments of the invention. The description and drawings serve to enable one skilled in the art to make and use the invention, and are not intended to limit the scope of the invention in any manner. In respect of the methods disclosed, the steps presented are exemplary in nature, and thus, the order of the steps is not necessary or critical.

The system for automating medical procedures (SAMP) according to the invention is a comprehensive and flexible system for automating medical, health and dental treatment procedures. Treatment procedures include any of modifying, removing, or delivering hard and soft bodily tissues, materials, prosthetic parts and biomedical devices; wherein the virtual modeling of the treatment area results in more precise treatment procedures when compared to state of the art procedures.

In the dental field, SAMP is conceived for restorative treatment but is modularly constructed and can be adapted and programmed for other dental procedures such as surgical implant planning and placement, crown and bridge work, fillings, orthodontics, laser and gum surgery, etc. Delivery of prosthetics, includes titanium implants, reconstructive and replacement parts, such as artificial joints, dental implants, artificial limbs; in biomedical devices, such as cardiac stents, pacemakers, etc. Modifying of hard and soft tissues includes milling of a tooth, orthopedic surgery, spinal fusions, tendon repairs, etc. Removal of hard and soft tissues includes biopsies, spinal taps, tumor removal, foreign matter material removal, etc. Delivery of hard and soft tissues includes collagen delivery, bone augmentation, genetic agents, etc. Delivery or removal of materials, includes anesthetics, nerve blocks, chemotherapeutic agents, etc.

The following description provides the background for dental treatments as they're currently provided and serves to illustrate how the SAMP invention facilitates the treatment, improves the results of the treatment and relieves the patients from much of the inconveniences associated with current procedures. The application in dentistry is discussed in detail only as an illustration of the system capabilities and not as a limitation. It should be clear to those skilled in the medical and robotic fields the wide range of applications of the SAMP invention to many other medical procedures.

Some features of the SAMP system also apply to other fields beyond the medical, health and dental applications and should be readily recognized especially by those contemplating the use of robotics and other computer controlled devices in their fields. The method of data collection from devices and sensors and the storage of data in central databases shared and populated by collaborating professionals, can be applied in non-medical computerized systems such as in manufacturing, warehousing, transportation, etc. Hence, the medical treatment procedure addressed herein could be any procedure for operating such computerized systems where data collection, centralization, collaboration and analysis is concerned.

Figure 1:
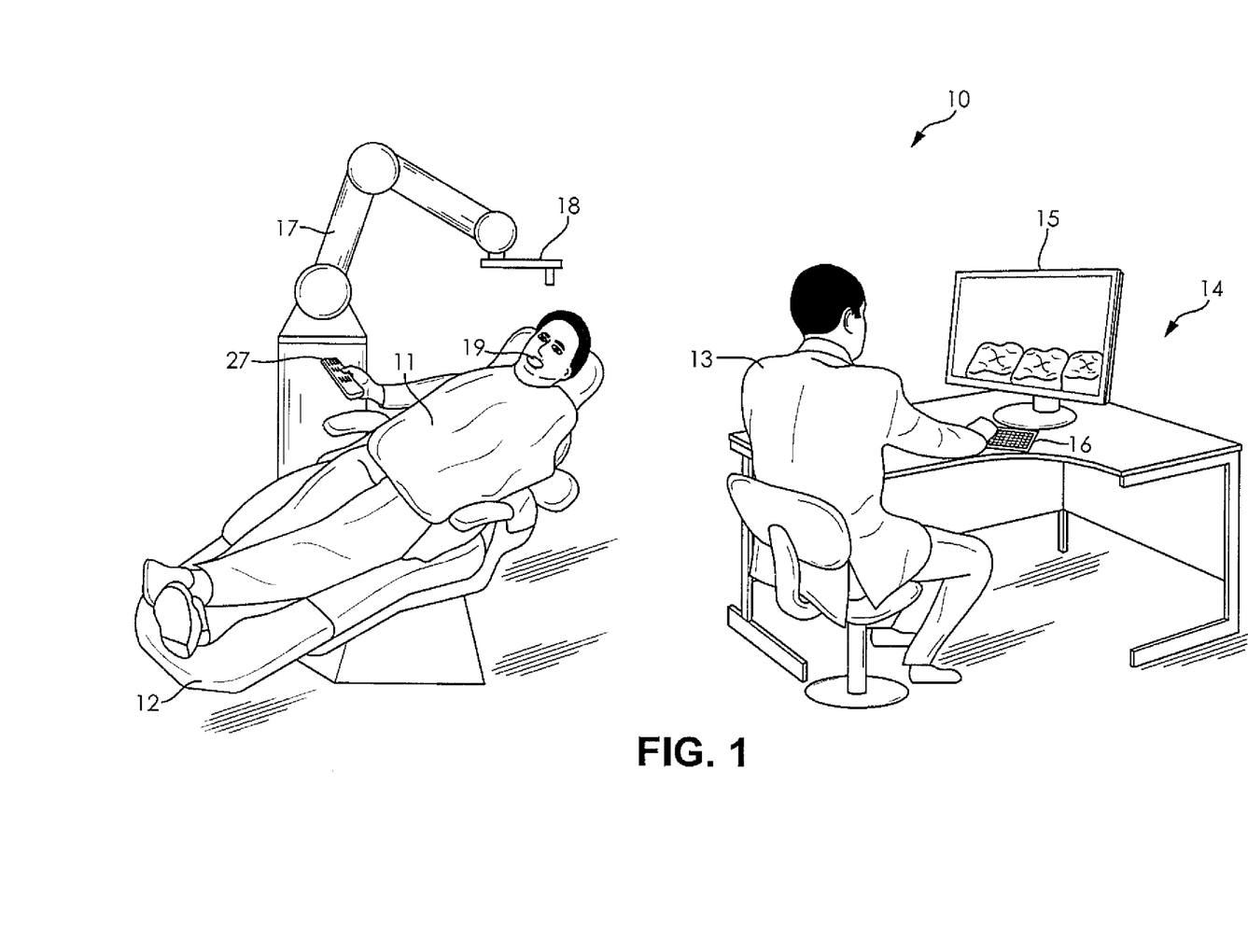
FIG. 1 is a perspective view of an overall system for automating medical/dental/health treatment procedures according to the invention illustrating a dental treatment example.

There is shown in FIG. 1 a schematic representation of the SAMP 10 for use in treating a dental patient 11 positioned on a patient table 12. A dentist/physician 13 is seated at a dentist/physician's station 14 for viewing a display 15 and interacting with a user interface 16. A robot arm 17 is positioned adjacent to the table 12 and carries a dental tool 18 for performing a pre-planned dental procedure in the mouth 19 of the patient 11.

Figure 2:
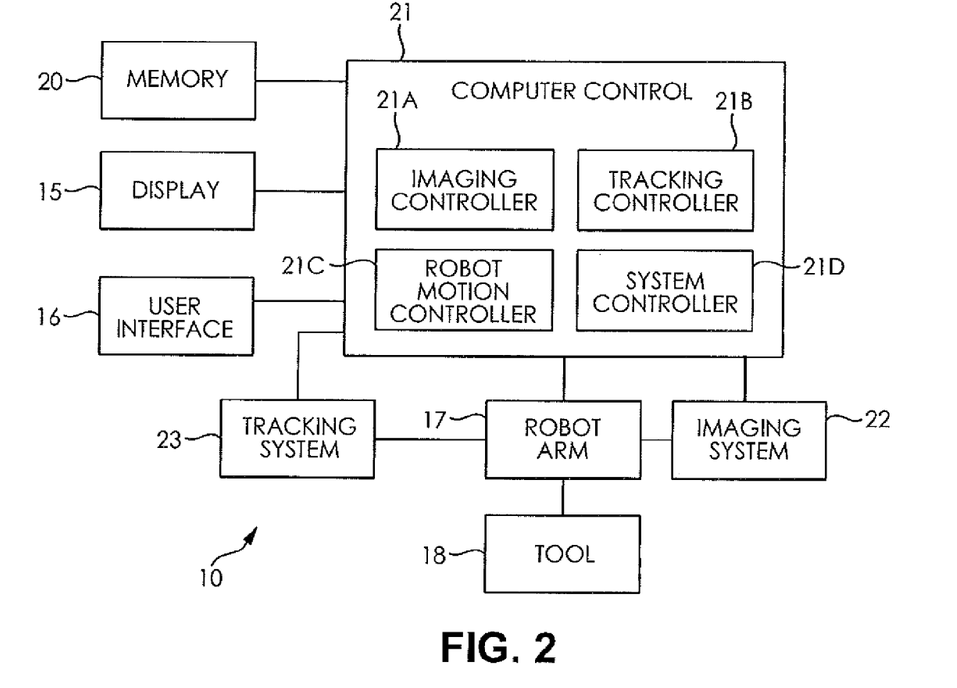
FIG. 2 is a block diagram of the components of the system according to the invention.

The basis for SAMP 10 is an imaging system, a tracking system, a robotic system, a networked database and a controlling computer system with supporting software. As shown in FIG. 2, the display 15, the user interface 16 (including any touch or touchless interface device such as a keyboard, a mouse, a touchpad, a motion gesture sensor, a microphone for voice recognition, or an imaging device) and a memory 20 are connected to a control computer 21 to form the controlling computer system. The supporting software is stored in the memory 20 and is run by the computer 21. The robot 17 is connected to the computer 21 for receiving movement command signals and signals to operate the tool 18. Also connected to and communicating with the computer 21 are an imaging system 22 and a tracking system 23.

The Imaging System: The imaging system 22 is used to generate a digital model of the dental treatment space and can display such digital model as a virtual image on the display screen 15 and communicate it to other computer controlled devices such as robots or machine tools. An example of a commercially available and widely used imaging system is the Lava™ Chairside Oral Scanner marketed by the 3M ESPE company. The imaging system 22 may also include cameras mounted on the tool that monitor the treatment space during the procedure and help guide the robot in response to movements detected during the procedure.

The model is generated by scanning the treatment space, the jaw and teeth, by means of a wand fitted with digital cameras, this is done manually or by the robot manipulating the wand. Several scanning passes are necessary to collect enough data images that are then assembled by specialized software into a 3-dimensional model of the treatment space. Markers, or fiducials, are placed within the space to help identify its coordinates and reference its location to other interacting devices. Scanners such as the 3M™ True Definition Scanner make it possible for dentists to take digital impressions. The file is sent via a data network to dental labs that can make traditional PFMs or CAD/CAM restorations including Lava™ Zirconia restorations.

As described below, the robot can manipulate the imaging device to generate the virtual model of the treatment space before and after the milling process. Markers can be affixed to the teeth in the treatment space to serve as a location reference for the robot, or specific teeth features can be used as markers. In general the imaging system can contain multiple sensors for imaging the teeth being treated. The sensors can be based on optical, ultrasonic, infrared, sonar or other wave or particle technologies, or other new developments fitting the purpose. In addition to on-board sensors, imaging from x-rays and CAT-scan data can be utilized for pre-treatment planning or during treatment.

The imaging system 22 can generate a 3D virtual image of the treatment space that can be recorded and projected on a display device. The recorded data can be used to generate 2-D, 3-D, or multi-dimensional physical or virtual models. The multi-dimensional model also includes data other than geometry, such as material properties, texture, color, etc. As common with digital images, they can be manipulated and viewed from different angles and differing magnifications. It is also common to interact with such images to superimpose other images or traces by means of tracing devices such as pointer, a computer mouse, or a light beam. Accordingly, the dentist can then identify a treatment path that, in his or her professional judgment will give the best milled surface for the tooth to be restored or fitted with a crown. The path is then digitized, referenced to the location markers, and stored for communication to the milling tool manipulator.

Other systems utilize navigation and imaging technologies to help the medical professional in planning for the procedures and providing real time guidance through visualization of the treatment space.

The Tracking System: The tracking system 23 tracks an object dynamically in real time with complete information about its location, orientation, and speed. Fiducials are placed in strategic locations within the treatment space such as a specific tooth or a rigid prop to the patient's jaw. Sensors are located at the end of a robotic arm that can recognize the different fiducials and track their location. Such sensors are well known to those skilled in the art and can be based on optical imaging, proximity measurements, capacitive measurements or other technologies. Imaging systems can use triangulation techniques with multiple cameras to provide distance and size measurements with a high rate of sampling to allow real time tracking. With end of the arm sensors the treatment space is tracked during the procedure and from within the treatment space itself. Therefore, SAMP 10 experiences no obstruction in the field of view of the sensors and allows the instruments a consistent registry with the fiducials that can be adjusted in real time in response to any movements. Provisions may be made to displace process associated obstructions such as debris or fluids.

Figure 3:
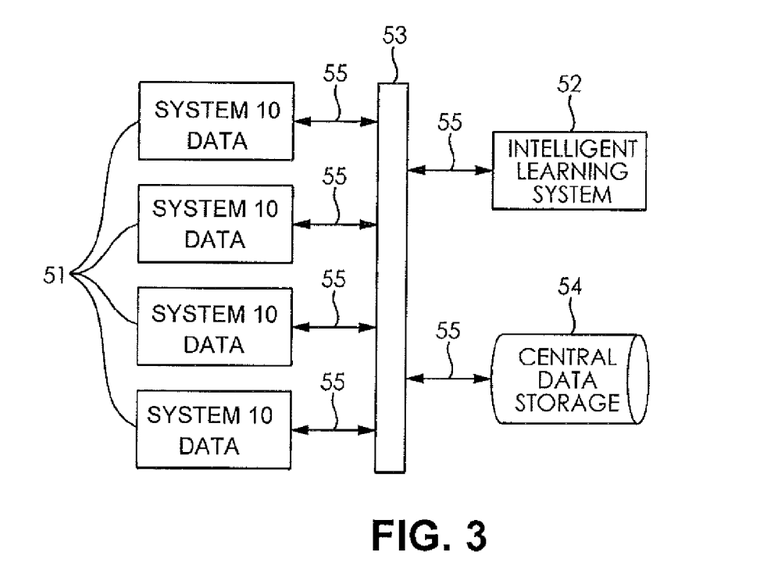
FIG. 3 shows a group of systems for automated medical procedures connected over a data network to a central data storage system accessed by an intelligent learning system.

The Robotic System: The robotic system consists preferably of an articulated arm 17 that can be affixed to a floor, a ceiling, a dental chair, the medical treatment table 11, or any other structure. The end of the arm 17 has attachments for instruments such as an imaging wand, a milling tool, or a dental drill. As shown in FIG. 3, a wrist 24 is attached at the end of the arm 17 and mounts the dental tool 18. The tool 18 is capable of carrying burs 25 of different sizes and shapes, usually made of diamond or tungsten carbide. The bur 25 can also be designed with specific hardness such as a nylon HDPE material to allow it to cut through decay and not cut through healthy tooth structure. Additional tool attachments can include a laser system, a tracking device, ultrasonic cleaning tips, dental implant attachments, root canal specific burs, etc. The robot 17 can have access to a tool changing magazine (not shown) fitted with all necessary instruments for applicable dental procedures as is common in many robotic applications.

During operation, the robot control system detects changes in the rotational speed and the operating torque of the mill or bur 25; these parameters together with other material removal parameters indicate changes in hardness due to decay or the presence of old restorations that may need to be replaced. The robotic system can then alter the path of the mill 25 to intelligently remove decay, e.g. following a path of least resistance or signal the professional of unexpected deviations.

The end of the robotic arm 17 is fitted with tracking sensors 26, such as digital cameras and proximity sensors of different technologies, to detect patient movement and is able to self-correct for any such movements or determine if the tool 18 should be shut off. This capability helps avoid enamel undercuts and possible patient injury. In contrast with the system shown in the '128 patent that tracks by means of an external camera system, the SAMP 10 according to the invention uses the end of the arm sensors 26 and allows the robot to track critical locations within the treatment space during its operation rather than from the outside. Therefore, the SAMP 10 experiences no obstruction in the field of view of the sensors 26 and allows the robot 17 to maintain consistent registry with the fiducials and respond in real time to any movements of the patient. The preferred sensor 26 includes one or more miniaturized digital cameras visualizing the relevant parts of the work space. Because of space restrictions around the end of arm tool, it's also possible to use fiber optics to form a collimating miniature lens at the end of an optical fiber and use another fiber to transmit light from a light source, such as used in endoscopes. Both fiber ends can be located at the surface of the tool and connected at their other ends remotely outside the treatment space to their electronic circuits. The electronic circuits can be designed to include the camera's pixel array, the retina, and a light source, such as a laser light emitting diode, LED. The electronics can be located inside or outside the robotic arm.

Other safety measures are present in the SAMP 10 to protect the patient during treatment. In the area of the mouth 19 where treatment is rendered to the patient protective barriers (not shown) are present to protect the tongue, cheek, and other surrounding tissues. The device can also have a built in mouth prop (not shown) to maintain the mouth open and not allow the patient to bite down into the tool 18 during operation. The SAMP 10 can also be programmed to stop the milling bur 25 immediately by initiating a quick electronic braking command, unlike a conventional dental drill that will not stop immediately due to inertia.

In addition, the patient can be provided with a hand-held safety shut off control 27 (FIG. 2) to allow the patient to stop the device in an emergency. A suction system (not shown) can also be provided to remove any coolant water.

In other procedures, a surgeon can virtually place a dental implant while avoiding vital structures such as a nerve. The location of the dental implant is then recorded for use in the generation of a corresponding treatment procedure and a treatment path to robotically place the actual implant. After the treatment path is generated according to the professionally developed treatment procedure, e.g. to remove an old filling or trace the path for milling a new crown, the treatment path is then communicated to the robotic arm to locate surface reference points, location markers, and automatically follow the path that the dentist had traced on the virtual image. In addition, the treatment path also defines the final restoration geometry and can be used not only to mill the tooth but to shape the crown as well. For a crown procedure, for example, the data can be communicated to a dental milling machine to produce the crown or filling even before the tooth has been touched and before the patient returns for the visit. A crown can then be readily fabricated and made ready for final application concurrently. A ceramic crown, gold crown, a composite filling, or any material can be utilized as the dentist and patient choose.

The Controlling Computer System: The SAMP 10 is controlled by the computer 21 that can have subsystems such as an imaging controller 21A, a tracking controller 21B, a robot motion controller 21C in addition to an overall system controller 21D as shown in FIG. 2. The computer 21 can include dedicated CPU's for each function or group of functions as in distributed processing, or an individual CPU handling all functions of the systems within a centralized control system. The imaging controller 21A is responsible for generating virtual images of the work space and allows the professional to manipulate the images and generate the path of the robot tool 18 during the procedure. The camera sensors 26 connected to the imaging system 22 can also be the same sensors used for tracking objects within the procedural space with their data shared and manipulated differently within the imaging and the tracking controllers 21A, 21B.

Figure 4A:
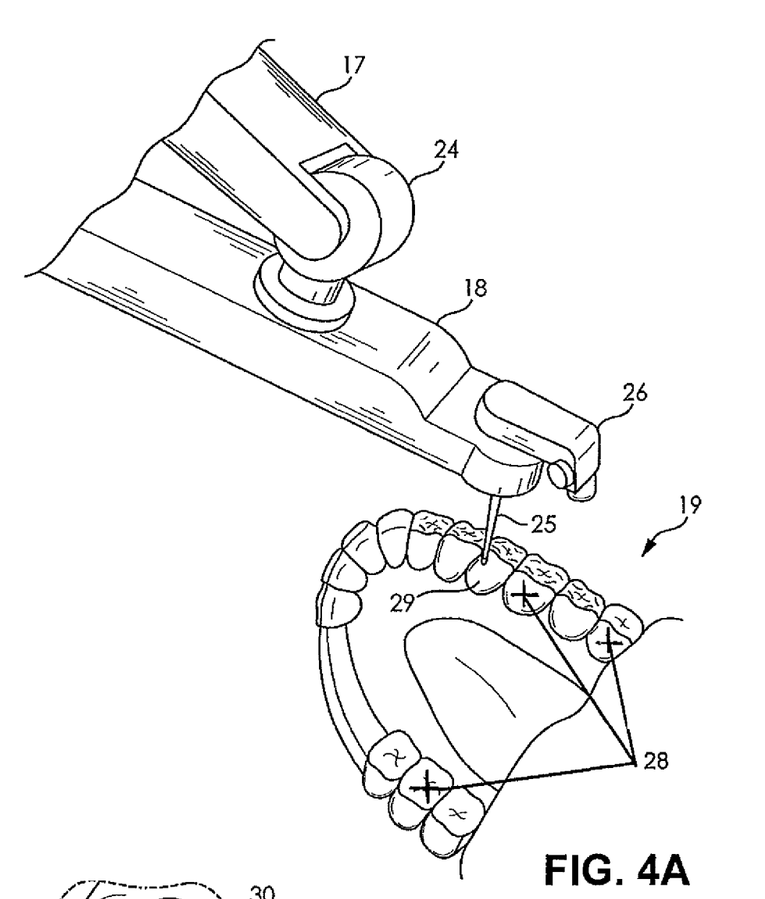
FIG. 4A is an enlarged perspective view of the treatment space shown in FIG. 1.
Figure 4B:
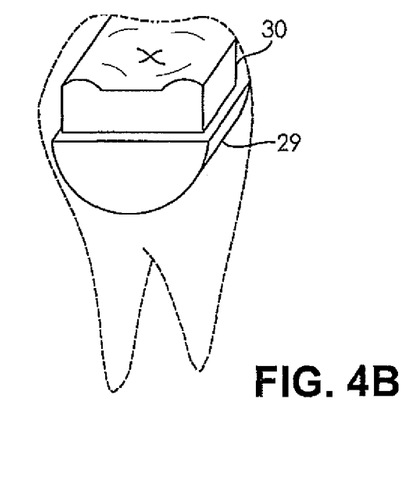
FIG. 4B is an enlarged perspective view of a tooth cut pattern for one of the teeth shown in FIG. 4A.

The sensors 26 can be, for example, one or more cameras for observing a plurality of reference points including fiducials or markers 28 (FIG. 4A) on the teeth in the patient's mouth 19. As shown in FIGS. 3 and 4A-4B, the reference points can be used to guide the dental tool 18 relative to a tooth 29 to perform a predetermined tooth-cut pattern 30. The sensor 26 may also be replaced with the imaging device that generates the virtual image of the workspace such as the 3M device. As customary with robot applications, the robot can be provided with a tool changing system wherein it picks up and deposits tools as required for each step in the medical procedure.

Figure 5:
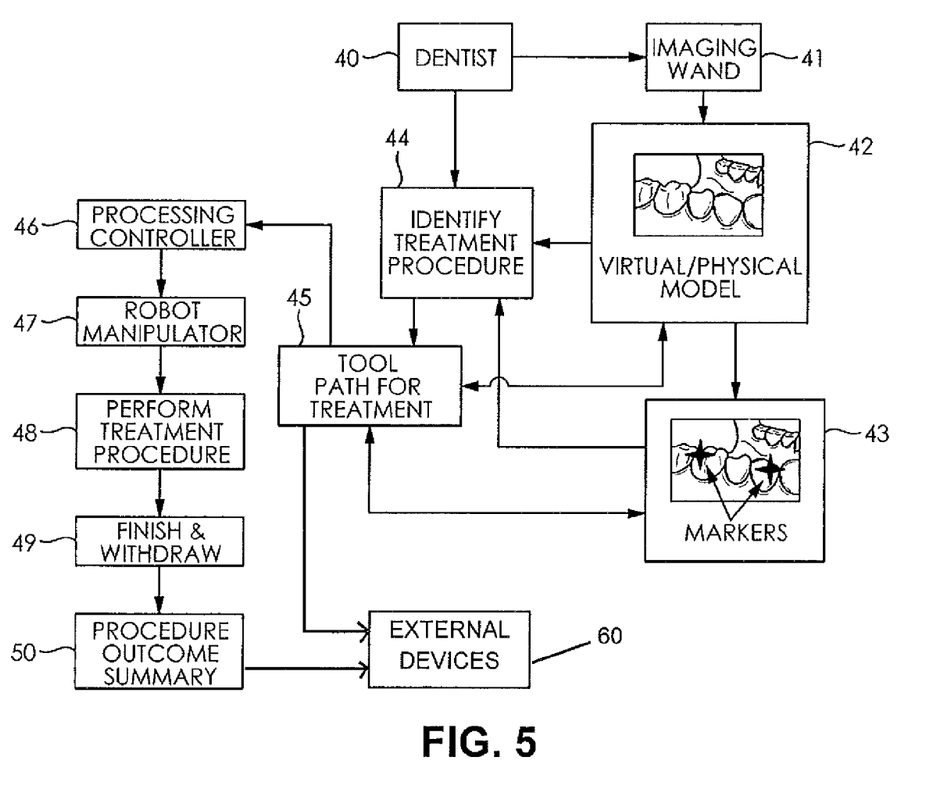
FIG. 5 is a flow diagram of the method for automating medical/dental/health treatment procedures according to the invention illustrating the dental treatment example.

There is shown in FIG. 5 a flow chart of the method according to the invention. In an initial step 40, the dentist 13 activates the SAMP 10 and performs a data collection step 41 with an input device 16 such as an imaging wand. Input data from the wand 16 is used by the computer 21 running the software stored in the memory 20 to create a virtual/physical model in a step 42 and to collect position data on the markers 28 in a step 43. The virtual/physical model is referenced to a local coordinate system based upon the configuration of the treatment area. Patient treatment data, such as diagnosis, material selection, treatment history, outcomes, etc., is collected and locally stored to be transmitted as needed, together with operational data related to the type and operation of devices and sensors, through the network to a central data system.

When the dentist 13 is ready, the computer 21 executes a step 44 using the model and marker position data stored in the memory 20 to permit the dentist to identify a treatment procedure including desired tool path features. The computer 21 then creates a tool path in a step 45 for implementing the identified treatment procedure. The system utilizes the tool path generated in step 45 to generate a data file of a virtual model of the tooth after the procedure is finished that may then be communicated to external devices 60 such as a milling machine or a 3D printer. Again, when the dentist 13 is ready, the computer 21 executes a processing controller step 46 wherein the system controller 21D directs the robot motion controller 21C to activate predetermined movements of the robot manipulator 17 in a step 47 to perform the selected treatment procedure in a step 48. When the treatment procedure is finished, the dental tool 18 is withdrawn from the treatment area in a step 49.

In an optional step 50 the procedure outcome is assessed and the data is also stored to be used in memory 20 or other networked memory for future reference and for the development of relevant databases for the patient, related diagnoses and treatment procedures by collaborating practitioners. The stored data is adaptive for analysis and for generating recommendations for enhancements of the treatment procedures and outcomes. The data is stored locally or centrally for sharing and for analysis by intelligent software systems. Also optionally, the system may utilize the tool path actually followed by the robot, as may be modified by the dentist during the procedure, to generate a data file of a virtual model of a crown, as an example, and communicate it to external devices 60 such as a milling machine or a 3D printer for fabrication. Other files of the Procedure outcome of step 50 may be communicated to other external devices for other purposes such as for data storage, sharing, and analysis.

There is shown in FIG. 3 a group of collaborating systems 51 for automated medical procedures, such as system 10 of FIG. 2, storing data generated while planning, performing, and terminating a medical procedure in a central data storage system 52 over a network 53. The central data storage system is also accessed by an intelligent learning system 54 that mines and analyzes the shared data and generates recommendations for possible improvements of the medical procedure based on the shared experiences of collaborating medical practitioners. Data is uploaded and downloaded, as indicated by the double arrows 55, between any of the systems and the network. Other devices may also access the network and interact with systems 10 and the central database when authorized.

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. A system for automating a medical process comprising:
   a memory storing a software program;
   a computer connected to the memory for running the software program;
   a user interface including a display connected to the computer for interacting with the computer and generating a visual representation of output data generated by the computer running the program;
   an imaging system connected to the computer for obtaining image data representing a configuration of a patient treatment space and fixed markers in the treatment space and storing the image data in the memory;
   a robot arm connected to the computer; and
   a medical tool mounted on the robot arm wherein when a human inputs a selected treatment procedure into the computer, the computer runs the software program to generate a tool path based upon the treatment procedure and the image data, and the computer operates the robot arm to move the medical tool along the tool path;

wherein the treatment space is defined by where the treatment procedure is performed by the medical tool and the fixed markers are located in the treatment space.

2. The system according to claim 1 wherein the user interface is one of an imaging wand, a keyboard, a computer mouse, a remote controller, an optical device or a wireless device.

3. The system according to claim 1 including a plurality of sensors mounted on the medical tool providing image feedback to the computer representing a position of the medical tool relative to the markers.

4. The system according to claim 3 wherein the sensors are one or more cameras.

5. The system according to claim 3 wherein the computer alters the tool path in response to movement in the treatment space detected in the image feedback.

6. The system according to claim 1 wherein the computer processes the image data to generate a virtual model or a physical model of the treatment space.

7. The system according to claim 6 wherein the virtual model or a physical model is referenced to a local coordinate system based upon the configuration of the treatment space.

8. The system according to claim 1 wherein the treatment space is located in a patient's mouth and the treatment procedure is one of imaging the treatment space, milling a tooth, drilling a tooth, placing material, installing a crown, installing orthodontic brackets, dental cleanings, root canals and installing an implant.

9. The system according to claim 1 including a shut-off control connected to the computer to stop the tool movement and withdraw the medical tool from the treatment space, the shut-off control being responsive to actuation by any of a patient initiative, patient movement, external influences or a system malfunction.

10. A method of automatically performing a medical treatment procedure in a treatment space comprising the steps of:
    operating an imaging system to obtain image data representing a configuration of a patient treatment space and fixed markers in the treatment space;
    generating a virtual model or a physical model of the treatment space having a local geometric coordinate system;
    selecting a treatment procedure to be performed in the treatment space;
    generating a tool path for movement of a medical tool carried by a robot arm based upon the treatment procedure and the virtual model or a physical model;
    actuating a computer to operate the robot arm to move the medical tool along the tool path thereby performing the treatment procedure; and
    withdrawing the medical tool from the treatment space at the end of the tool path to finish the treatment procedure;
    wherein the treatment space is defined by where the treatment procedure is performed by the medical tool and the fixed markers are located in the treatment space.

11. The method according to claim 10 including relating the local coordinate system to the fixed markers.

12. The method according to claim 10 wherein the treatment procedure is one of (1) modifying hard and soft bodily tissues, materials, prosthetic parts and biomedical devices, (2) removal of hard and soft bodily tissues, materials, prosthetic parts and biomedical devices, or (3) delivery of hard and soft bodily tissues, materials, prosthetic parts and biomedical devices; wherein the virtual modeling of the treatment area results in more precise treatments.

13. The method according to claim 10 including storing the tool path and parameters of the treatment procedure including patient data, devices data, providers' data and materials data in a memory connected to the computer.

14. The method according to claim 13 including analyzing the data by an intelligent learning system to generate possible enhancements to the treatment procedures.

15. The method according to claim 10 including the computer altering the tool path in response to movement in the treatment space detected by a tracking system.

16. The method according to claim 10 including moving the medical tool to a vicinity of the treatment space, locating the markers and moving the medical tool to a start of the tool path based upon positions of the markers.

17. The method according to claim 16 including locating the markers by one of touching the markers with the medical tool and by acquiring an image of the markers with a camera.

18. The method according to claim 10 including displaying a representation of the physical model as a virtual model and displaying the tool path on a display connected to the computer.

19. The method according to claim 18 wherein the tool path is generated by tracing the tool path on the virtual model by means of an input device interacting with the display.

20. The method according to claim 13 wherein the computer stores the data in a central data system and populates a medical database over a data network for sharing with other computers and devices of collaborating professionals.

21. The method according to claim 20 including analyzing the data stored in the central data system by an intelligent learning system to generate possible enhancements to the treatment procedures.

22. A method for populating databases, wherein a computer system operates devices, including data collecting sensors, and performs a procedure comprising the steps of:
    connecting the computer system to the devices;
    inputting a procedure into the computer system;
    inputting environment data including data identifying the devices, data collecting sensors, objects and parameters of the procedure, into the computer system, wherein the devices include a tool for performing the procedure;
    commanding the computer system to operate the devices autonomously and perform the procedure;
    collecting operational data from the devices and data collecting sensors;
    recording outcome data describing the results of the procedure;
    generating a data set comprising the operational data, the environment data, and the outcome data; and
    adding the data set to a database in a memory connected to the computer.

23. The method according to claim 22, wherein the computer stores the data set in a central database system for sharing with other computers and devices contributing other data sets over a network.

24. The method according to claim 23 including analyzing the data sets shared in the central data system by an intelligent learning system to generate possible enhancements to the procedure.

* * * * *